United States Patent
Roby et al.

(10) Patent No.: US 10,945,862 B2
(45) Date of Patent: Mar. 16, 2021

(54) JOINT REAMING DEVICES AND METHODS

(71) Applicant: Biomet Manufacturing, LLC, Warsaw, IN (US)

(72) Inventors: Keith A. Roby, Jersey City, NJ (US); John Chernosky, Brick, NJ (US); Joseph Markham, Hillsborough, NJ (US); Robert G. Deluca, Bethlehem, PA (US)

(73) Assignee: Biomet Manufacturing, LLC, Warsaw, IN (US)

( * ) Notice: Subject to any disclaimer, the term of this patent is extended or adjusted under 35 U.S.C. 154(b) by 259 days.

(21) Appl. No.: 15/973,601

(22) Filed: May 8, 2018

(65) Prior Publication Data

US 2018/0333276 A1    Nov. 22, 2018

Related U.S. Application Data

(60) Provisional application No. 62/508,768, filed on May 19, 2017.

(51) Int. Cl.

| | |
|---|---|
| *A61F 2/46* | (2006.01) |
| *A61B 17/16* | (2006.01) |
| *A61F 2/40* | (2006.01) |
| *A61B 17/17* | (2006.01) |
| *A61B 17/56* | (2006.01) |
| *A61B 17/88* | (2006.01) |
| *A61B 90/00* | (2016.01) |

(52) U.S. Cl.
CPC ........ *A61F 2/4612* (2013.01); *A61B 17/1615* (2013.01); *A61B 17/1659* (2013.01); *A61B 17/1684* (2013.01); *A61B 17/1778* (2016.11); *A61F 2/4081* (2013.01); *A61B 17/1697* (2013.01); *A61B 17/8872* (2013.01); *A61B 17/8883* (2013.01); *A61B 17/8897* (2013.01); *A61B 2017/1602* (2013.01); *A61B 2017/564* (2013.01); *A61B 2090/036* (2016.02)

(58) Field of Classification Search
CPC .. A61F 2/46; A61F 2/4612; A61F 2/40; A61F 2/4081; A61B 17/16; A61B 17/1659; A61B 17/1615; A61B 17/1778
See application file for complete search history.

(56) References Cited

U.S. PATENT DOCUMENTS

| | | | | |
|---|---|---|---|---|
| 2009/0270865 | A1* | 10/2009 | Poncet | A61B 17/1659 606/87 |
| 2016/0045207 | A1 | 2/2016 | Kovacs et al. | |
| 2018/0008293 | A1* | 1/2018 | Kovacs | A61B 17/1684 |

FOREIGN PATENT DOCUMENTS

| | | |
|---|---|---|
| WO | 2018213054 | 11/2018 |

OTHER PUBLICATIONS

"International Application Serial No. PCT US2018 031467, International Search Report dated Aug. 21, 2018", 5 pgs.
"International Application Serial No. PCT US2018 031467, Written Opinion dated Aug. 21, 2018", 6 pgs.

(Continued)

*Primary Examiner* — Christopher J Beccia
(74) *Attorney, Agent, or Firm* — Schwegman Lundberg & Woessner, P.A.

(57) ABSTRACT

Surgical instrumentation and methods for reaming a bone are disclosed. In some cases, the bone is a glenoid of a shoulder. The surgical instrumentation can include a bushing that acts as a guide for a reamer, which reams the bone.

19 Claims, 9 Drawing Sheets

(56) References Cited

OTHER PUBLICATIONS

"International Application Serial No. PCT/US2018/031467, International Preliminary Report on Patentability dated Nov. 28, 2019", 8 pgs.

"European Application Serial No. 18727519.3, Response to Communication pursuant to Rules 161(1) and 162 EPC filed Jul. 31, 2020", 10 pgs.

* cited by examiner

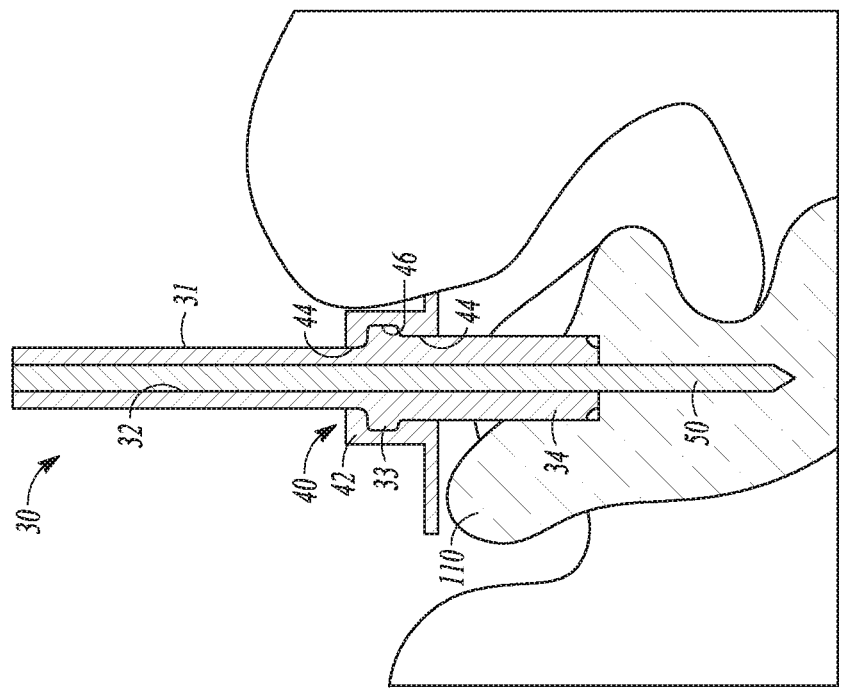
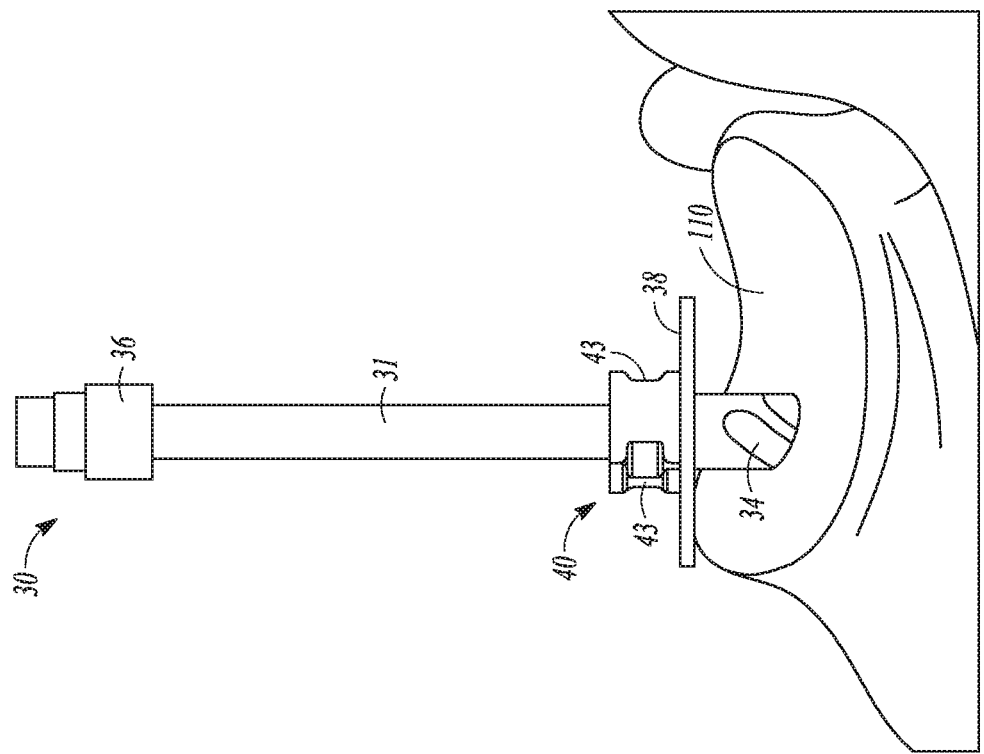

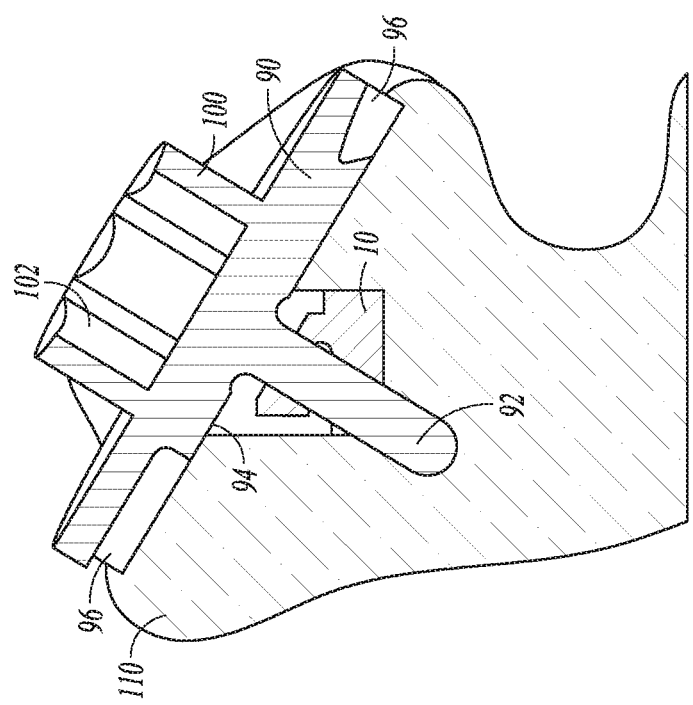
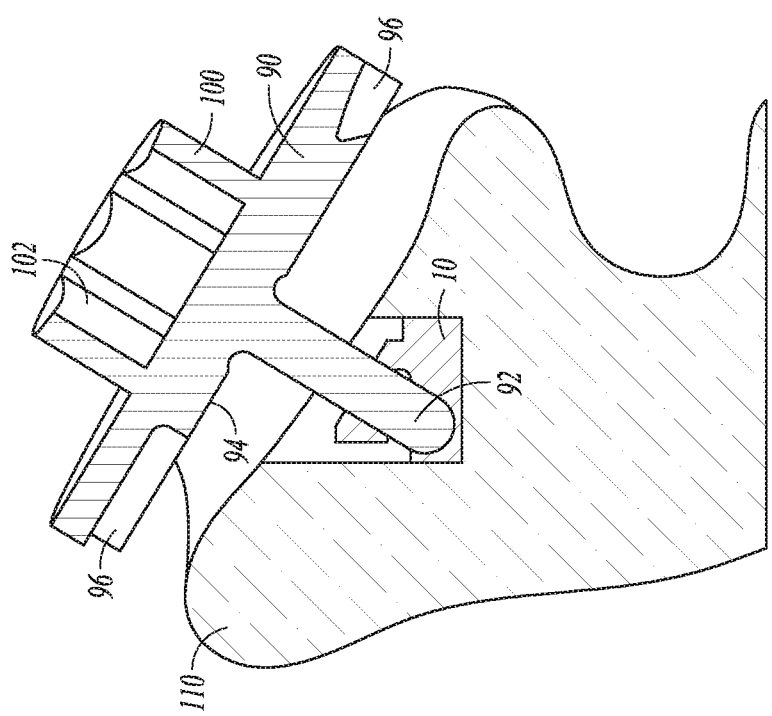

JOINT REAMING DEVICES AND METHODS

PRIORITY APPLICATIONS

This application claims the benefit of priority to U.S. Provisional Application Ser. No. 62/508,768, filed May 19, 2017, the content of which is hereby incorporated by reference in its entirety.

FIELD OF THE DISCLOSURE

The present disclosure relates to joint replacement systems, including joint replacements, instruments, and methods of use thereof. Specifically, the present disclosure relates to bone reaming devices and systems for preparing a joint for receiving a joint replacement.

BACKGROUND

In some cases, shoulder pain and degradation results in a need for a shoulder replacement or other repair. Typically, in the case of a replacement, a patient's glenoid and/or humerus are reamed and prosthetic components are placed on the glenoid and/or humerus to repair normal function to the patient's shoulder. In some instances, a traditional shoulder replacement is undertaken whereby a prosthetic humeral head is implanted in the patient's humerus and/or a concave glenoid component is implanted in the patient's glenoid, which interacts with the prosthetic humeral head. Other patients require a reverse shoulder replacement whereby a glenosphere is attached to the patient's glenoid and a prosthetic humeral socket is attached to the patient's humerus for interacting with the glenosphere.

Prior to attaching a glenoid component, whether a traditional concave component or a glenosphere, the glenoid is typically prepared and any defect(s) thereon removed or repaired. This might involve reaming the glenoid surface so that it is prepared to receive the concave glenoid component/glenosphere. Yet, improper reaming of the glenoid can result in complications for the patient. For instance, if the glenoid component or glenosphere is inserted at a sub-optimal angle, features of the glenoid component or glenosphere (e.g., a fixation post or screw) can penetrate the glenoid vault.

The present disclosure provides shoulder replacement instrumentation, methods, and implants used to properly insert a glenoid component or glenosphere onto a glenoid.

SUMMARY

To better illustrate the system disclosed herein, a non-limiting list of examples is provided here:

Example 1 includes an orthopedic system comprising an implantable body with an internal bore extending through the body, and a reamer having a cutting surface and a shaft, wherein the shaft is insertable into the internal bore of the body for guiding the reamer during reaming of a bone.

In Example 2, the system of Example 1 can optionally include wherein the body has a set of sidewalls and the internal bore is angled relative to the sidewalls.

In Example 3, the system of Example 2 can optionally include wherein the angle of the internal bore is anywhere between about 5-45°.

In Example 4, the system of any one of or any combination of Examples 1-3 can optionally include wherein the cutting surface of the reamer comprises cutting teeth configured to cut away bone.

In Example 5, the system of any one of or any combination of Examples 1-4 can optionally include wherein the implantable body has an external surface with at least a first projection configured to engage bone and prevent back-out of the implantable body when implanted.

In Example 6, the system of any one of or any combination of Examples 1-5 can optionally include wherein the implantable body is sized and shaped so as to be insertable into a bore formed in bone, the implantable body being threaded, having an external projection configured to engage bone, or being configured to be press-fit into the bone bore to secure the implantable body in the bone bore.

In Example 7, the system of any one of or any combination of Examples 1-6 can optionally include wherein the implantable body has a top face and a bottom face and the top face is angled relative to the bottom face.

In Example 8, the system of any one of or any combination of Examples 1-7 can optionally further comprise a drill having a cutting section that is sized and shaped to form a bore in bone that is substantially the same size and shape as the size and shape of the implantable body.

Example 9 includes a method of reaming bone comprising forming a bore in bone, implanting an implantable body into the bone bore, the implantable body having an internal bore extending through the body, inserting a portion of a reamer having a cutting surface through the internal bore of the implantable body to guide the reamer against the bone, and reaming the bone with the cutting surface of the reamer while the portion of the reamer is inside the internal bore.

In Example 10, the method of Example 9 can optionally include wherein the bone is a glenoid and the internal bore of the implantable body is angled so as to guide the cutting surface of the reamer into the glenoid at an angle.

In Example 11, the method of any one of or any combination of Examples 9-10 can optionally further comprise inserting a shaft of the reamer through the internal bore of the implantable body to guide the reamer against the bone.

In Example 12, the method of any one of or any combination of Examples 9-11 can optionally further comprise attaching an inserter to the implantable body and inserting the implantable body into the bone bore using the inserter.

In Example 13, the method of any one of or any combination of Examples 9-12 can optionally include wherein the implantable body has a set of sidewalls and the internal bore is angled relative to the sidewalls.

In Example 14, the method of Example 13 can optionally include wherein the angle of the internal bore is anywhere between about 5-45°.

In Example 15, the method of any one of or any combination of Examples 13-14 can optionally further comprise forming the bone bore to a certain depth depending upon the angle of the internal bore of the implantable body.

In Example 16, the method of Example 15 can optionally further comprise forming the bone bore to a depth of anywhere between about 5-10 mm if the angle of the internal bore is anywhere between about 5-15°, forming the bone bore to a depth of anywhere between about 10-15 mm if the angle of the internal bore is anywhere between about 15-25°, or forming the bone bore to a depth of anywhere between about 12.5-17.5 mm if the angle of the internal bore is anywhere between about 25-35°.

In Example 17, the method of any one of or any combination of Examples 9-16 can optionally further comprise selecting a first implantable body having an internal bore from a plurality of implantable bodies each having an internal bore, each of the internal bores being angled, wherein the bone is a glenoid and the selection is made so that the angle of the internal bore of the first implantable body guides the reamer against the glenoid to ream the glenoid at a suitable angle taking into account a natural angle of an articulating surface of the glenoid.

Example 18 includes a method of reaming a glenoid comprising determining an angle of an articulating surface of the glenoid, selecting a first implantable body from a plurality of implantable bodies, each implantable body having an angled internal bore, forming a bore in the glenoid, implanting the first implantable body in the bore in the glenoid, and inserting a reamer having a cutting surface into the internal bore of the first implantable body so that the cutting surface is applied against the glenoid at an angle.

In Example 19, the method of Example 18 can optionally include wherein the angle at which the reamer is applied against the glenoid has a correlation to the angle of the articulating surface of the glenoid.

In Example 20, the method of any one of or any combination of Examples 18-19 can optionally include wherein the angle at which the reamer is applied against the glenoid substantially matches the angle of the articulating surface of the glenoid.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein:

FIG. 2A is a side view of a drill and depth gauge being inserted into a glenoid.

FIG. 2B is a cross-sectional view of the drill and depth gauge of FIG. 2A.

FIG. 6A is a cross-sectional view of the bushing of FIGS. 1A-D being used with a reamer to ream a glenoid surface.

FIG. 6B is a subsequent cross-sectional view of FIG. 6A in which the reamer is advanced to ream the glenoid.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

In describing the examples of the invention(s) illustrated and to be described with respect to the drawings, specific terminology will be used for the sake of clarity. However, the invention(s) is not intended to be limited to any specific terms used herein, and it is to be understood that each specific term includes all technical equivalents.

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body or a body structure that divides the body or body structure into right and left halves. In addition, the terms implant and prosthesis, and variations thereof, can be used interchangeably.

The present disclosure is directed at reaming instruments and methods used to prepare bone for a joint replacement. In an example, a bushing can be placed in the glenoid and used to guide a reaming device to ream the glenoid so that, for example, the glenoid can receive a glenoid prosthetic component.

Figure 1A:
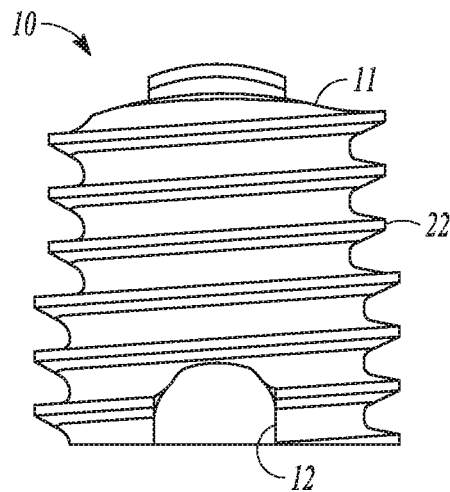
FIGS. 1A-D are front (1A), cross-sectional (1B), perspective (1C), and side (1D) views of a bushing according to an example of the disclosure.
Figure 1B:
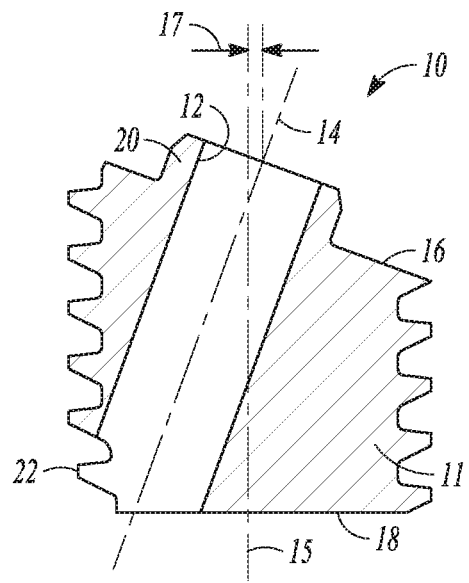

Referring to FIGS. 1A-D, a bushing 10 is shown. Bushing 10 can include a body 11 that has external threading 22 for threading body 11 into a hole formed in a glenoid of a patient. Further, body 11 can have top and bottom faces 16, 18 and a projection 20 extending from top face 16. External threading 22 can include a single-lead thread or multi-lead threads. Top face 16 can be angled relative to bottom face 18, which can be substantially flat in an example. A bore 12 can be formed through body 11 that extends partly or entirely through body 11 along an axis 14. Axis 14 can intersect a central axis 15 of body 11 at a distance below a proximal-most point of projection 20. Stated differently, an offset 17 can be established between axis 14 and central axis 15 at the proximal-most surface of projection 20, as shown in FIG. 1B. In an example, offset 17 can be anywhere between about 0.005 mm to about 0.25 mm.

Referring still to FIG. 1B, bore 12 can be angled through body 11 and, in an example, can have an angle that substantially matches the angle of top face 16. For instance, bore 12 and/or top face 16 can be angled by anywhere between about five degrees to about forty five degrees (5°-45°). In a specific example, bore 12 and/or top face 16 can be angled by about ten degrees (10°), about twenty degrees (20°), or about thirty degrees (30°). As described in more detail below, the angle of bore 12 and/or top face 16 can dictate the angle at which reamer 90 approaches and reams a patient's glenoid.

Figure 1C:
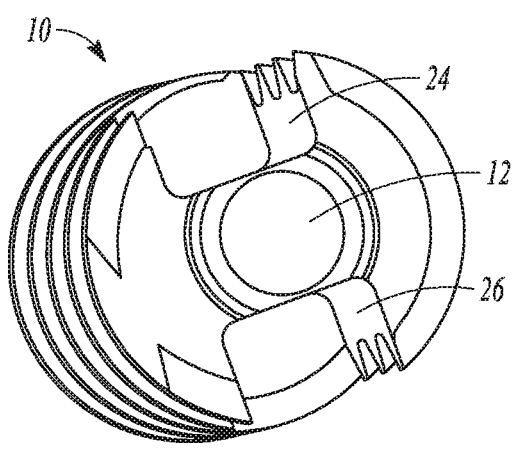
Figure 1D:
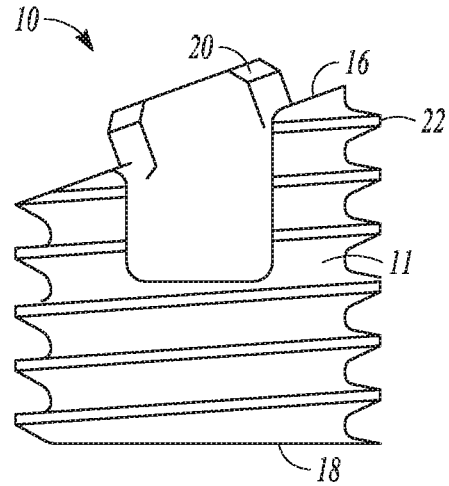

Referring to FIG. 1C-1D, body 11 of bushing 10 can also include first and second channels or cutouts 24, 26 for interacting with a bushing inserter 60, in an example, first and/or second cutout 24, 26 can extend partway along body 11 from top face 16 towards bottom face 18, but stops short of bottom face 18. Thus, a portion of external threads 22 can extend between bottom face 18 and first and/or second cutouts 24, 26. In other examples, cutouts 24, 26 can extend entirely to bottom face 18. First and second cutouts 24, 26 can be arranged on diametrically opposite sides of body 11 of bushing 10.

A drill 30 is shown in use in FIGS. 2A-B. Drill 30 can have a proximal section 36 that has any number of features for engaging with a driving instrument (not shown). For instance, proximal section 36 can be formed as a male hexagonal projection or a female hexagonal recess for engaging with a male/female part of a driving instrument (not shown), or it can be formed as a bayonet connection for engaging with the driving instrument (not shown). The driving instrument can be a powered driving instrument, such as a power drill, or it can be a manual driving instrument (e.g., a T-handle or a straight handle). Drill 30 can also have a distal cutting section 34 that is formed with cutting flutes or edges configured to cut bone.

Drill 30 can further have a shaft 31 that has a single or multiple projections 33 on shaft 31 for engaging with a depth stop 40. Depth stop 40 can have a body 42 that is hollow and can include a flange 38. Hollow body 42 can have first bore parts 44 that each has a diameter substantially equal to or only slightly greater than a diameter of shaft 31, and a second bore part 46 that has a diameter substantially equal to or only slightly greater than a diameter of shaft 31 at projection 33. As such, depth stop 40 can engage shaft 31 of drill 30 and be substantially locked in an axial direction relative to shaft 31 since projection 33 can fit within second bore part 46. In an example, as shown in FIG. 2A, body 42 can also include a single or multiple openings 43 for engaging with the single or multiple projections 33. Such engagement can act to substantially lock depth stop 40 rotationally relative to shaft 31 of drill 30. Drill 30 can also be cannulated via a bore 32 through shaft 31 so as to be able to receive and be guided over a fixation pin 50 with a sharp tip capable of penetrating bone (e.g., a K-wire).

FIGS. 2A-B illustrate drill 30 and depth stop 40 inserted over a fixation pin 50. In particular, drill 30 and depth stop 40 can be inserted over fixation pin 50, which has previously been inserted into a glenoid 110 of a patient. A certain distance of cutting section 34 of drill 30 can extend away from depth stop 40, for example anywhere between about five millimeters to about twenty millimeters (5-20 mm). In a particular example, the distance can correlate to the angle of bore 12 of bushing 10. For instance, the distance can be eight millimeters (8 mm) when the angle of bore 12 is ten degrees (10°), the distance can be ten and a half millimeters (10.5 mm) when the angle of bore 12 is twenty degrees (20°), or the distance can be thirteen and a quarter millimeters (13.25 mm) when the angle of bore 12 is thirty degrees (30°). Of course, these distances are exemplary and other distances, which correlate with the angle of bore 12, are contemplated. Thus, drill 30 can be inserted over fixation pin 50 as shown in FIGS. 2A-B until depth stop 40 contacts a portion of the patient's glenoid 110 and ceases drilling further into glenoid 110. In an example, the resulting bore formed in glenoid 110 can therefore approximate the distance of cutting section 34 that extends from depth stop 40 (e.g., anywhere between about five millimeters to about twenty millimeters (5-20 mm)).

Figure 3B:
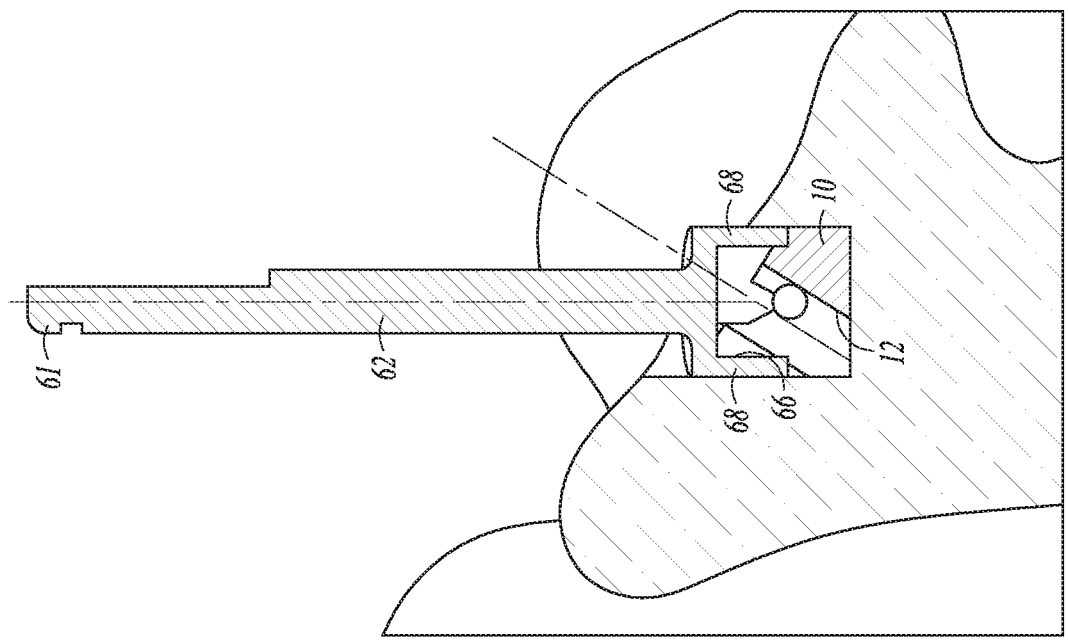
FIG. 3B is a cross-sectional view of the bushing and bushing inserter of FIG. 3A.
Figure 3A:
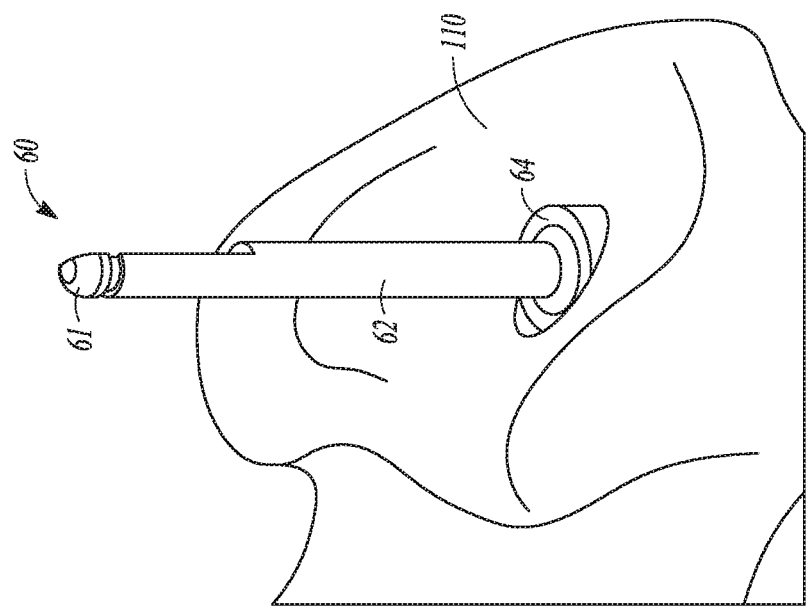
FIG. 3A is a perspective view of the bushing of FIGS. 1A-D being inserted into a hole in a glenoid using an inserter.

FIGS. 3A-B illustrate a bushing inserter 60 used to insert bushing 10 into a bore in glenoid 110. As shown, bushing inserter 60 can have a shaft 62 and an attachment head 64 configured to engage with bushing 10. Shaft 62 can have a proximal section 61 that is configured to engage with a driving instrument (not shown) for rotating shaft 62, and thus bushing inserter 60. Proximal section 61 can, for example, be shaped to non-rotationally engage with a female part of a driving instrument (not shown), which can be manual (e.g., T-handle or straight handle) or powered (e.g., power drill). Attachment head 64 can have a diameter that is greater than a diameter of shaft 62 and a bore 66 sized to receive bushing 10. For instance, bore 66 can be sized to receive projection 20 of bushing 10 and/or part of body 11 of bushing 10. Attachment head 64 can further include a single or multiple arms 68 that are sized and shaped to be inserted into first and/or second cutouts 24, 26 of bushing 10. Attachment head 64 can therefore engage bushing 10 and securely lock bushing 10 to bushing inserter 60, both longitudinally and rotationally. Bushing 10 is shown schematically in FIGS. 3A-B, and thus, some features thereof might appear to be missing.

Referring still to FIGS. 3A-B, bushing inserter 60 can be attached to bushing 10 and used to drive bushing into a bore in glenoid 110 after the same is formed with drill 30, as discussed with reference to FIGS. 2A-B. In the inserted position, bottom face 18 of bushing 10 can contact a bottom face of the bone bore formed using drill 30, and top face 16 of bushing 10 can be presented for further use, as detailed below. Axis 14 of bushing 10 can extend into glenoid 110 at an angle that is the same as the angle of bore 12 of bushing 10, as shown in FIG. 3B.

Figure 4B:
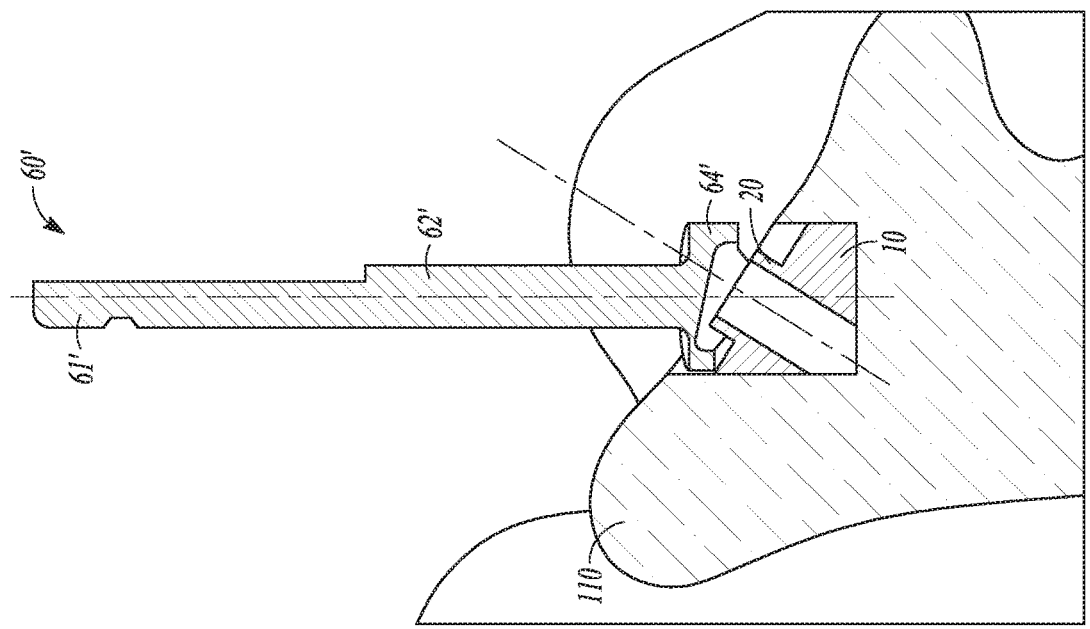
FIG. 4B is a cross-sectional view of the alternate bushing and bushing inserter of FIG. 4A.
Figure 4A:
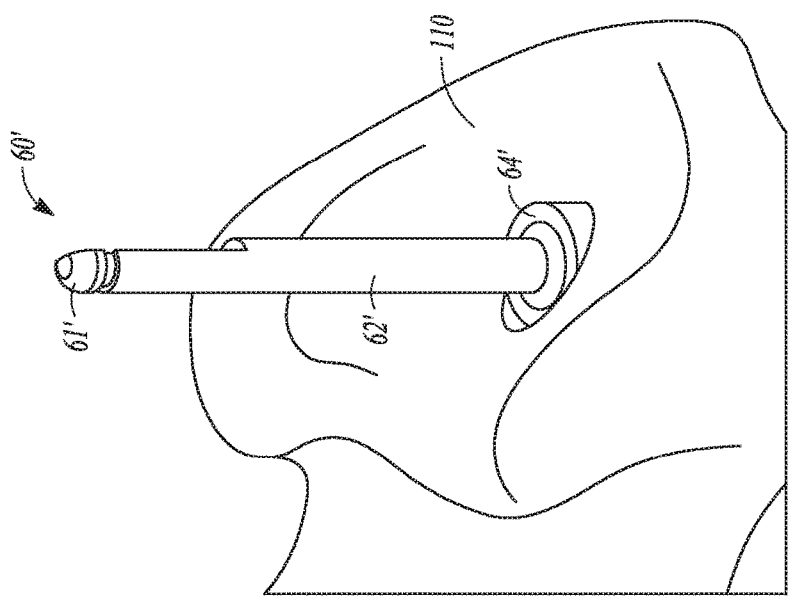
FIG. 4A is a perspective view of an alternate bushing being inserted into a hole in a glenoid using an alternate bushing inserter.

FIGS. 4A-B illustrate an alternate bushing inserter 60'. Like reference numerals are used for like elements in this example, except that a prime designation is appended to the numerals. Thus, bushing inserter 60' can be the same as bushing inserter 60, except as described below.

Bushing inserter 60' can have a bore 66' in attachment head 64' that is sized and shaped to receive projection 20 of bushing 10, but part or all of attachment head 64' can either incorporate a single or multiple magnets and/or be formed of a magnetic material. Further, projection 20 and/or top face 16 of bushing 10 can likewise incorporate a single or multiple magnets and/or be formed of a magnetic material. Thus, when attachment head 64' is brought close to bushing 10, attachment head 64' can attach to projection 20 and/or top face 16 of bushing 10 through a magnetic connection. The magnetic connection can be sufficiently strong so as to lock bushing inserter 60' to bushing 10 both rotationally and longitudinally. Alternatively, projection 20 can be shaped to non-rotationally engage with bore 66' of bushing inserter 60' while the magnetic connection can secure bushing inserter 60' to bushing 10 longitudinally. For instance, projection 20 can be oval, polygon shaped, or hexagonally shaped to non-rotationally engage with a likewise shaped bore 66'. Bushing inserter 60' is shown in use in FIGS. 4A-B inserting bushing 10 into a bore in glenoid 110, much the same as in FIGS. 3A-B. Here again, bushing 110 is shown schematically and some of the details thereof (e.g., threads) are omitted.

A reamer 90 is shown in FIGS. 6A-B that can interact with bushing 10 once implanted in glenoid 110. Reamer 90 can have a cutting side or face 94 defined by a single or multiple cutting flanges 96 and a shaft 92 extending outwards relative to cutting side 94. A projection 100 having a drive engagement 102, in an example in the form of a hexagonal recess, can be formed on reamer 90. In other examples, drive engagement 102 can be any other alternate drive engagement feature, for instance a hexagonal projection, a polygon-shaped recess or projection, or any structural feature capable of engaging with a driving instrument (not shown) for rotating reamer 90. Cutting face 94 can have cutting projections or teeth 98 extending therefrom that are configured to cut bone as reamer 90 is driven into glenoid 110. Cutting teeth 98 can present sharp edges or other features designed to cut or scrape away bone.

Figure 6C:
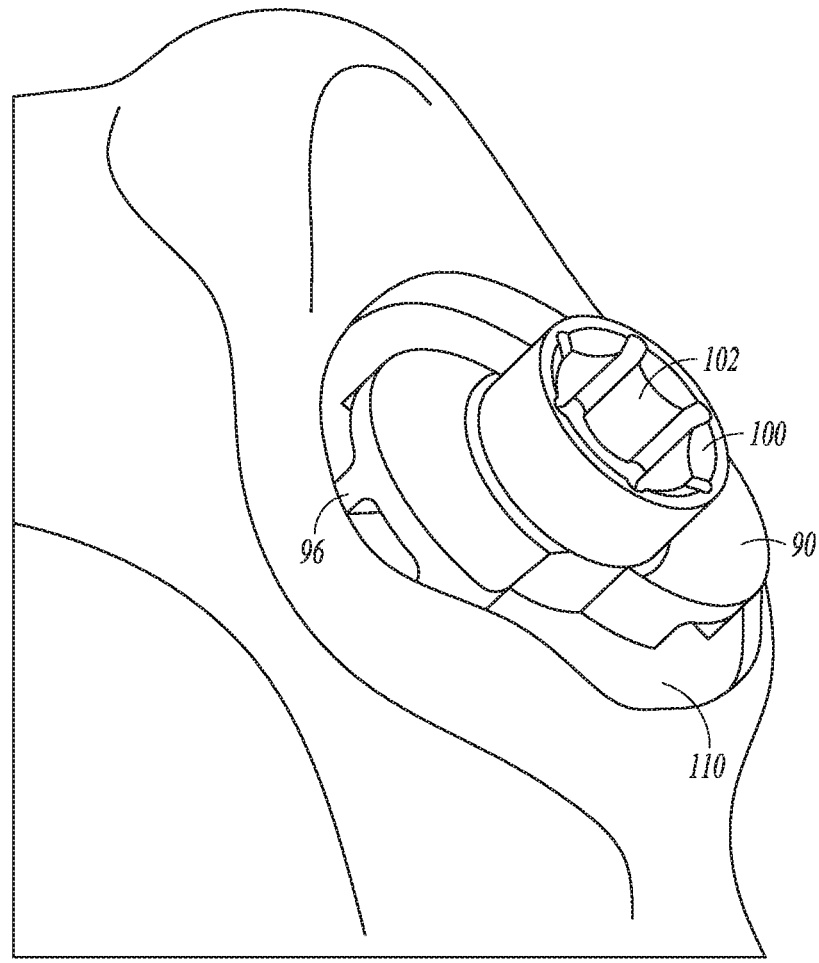
FIG. 6C is a perspective view of the glenoid surface after reaming with the reamer of FIGS. 6A-B.

As shown in FIGS. 6A-C, shaft 92 of reamer 90 can be inserted into bore 12 of bushing 10 and guided into glenoid 110 to ream glenoid 110 at a particular angle. The reaming angle can correspond to the angle of bore 12 of bushing 10. Thus, as an example, the reaming angle can be ten degrees (10°), twenty degrees (20°), thirty degrees (30°), or any angle that corresponds substantially to the angle of bore 12 of bushing 10. FIG. 6C shows glenoid 110 after reaming via reamer 90.

Figure 5B:
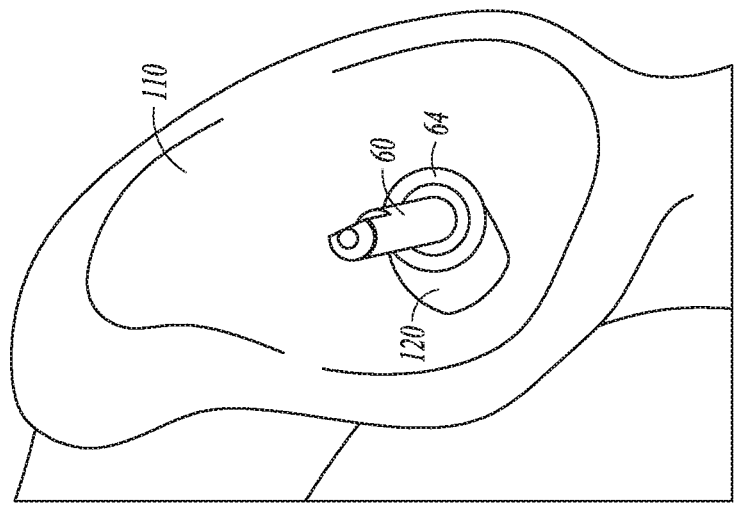
FIG. 5B is a perspective view of the bushing inserter of FIGS. 3A-B and a resulting hole formed in the glenoid using the cleanup reamer of FIG. 5A.
Figure 5A:
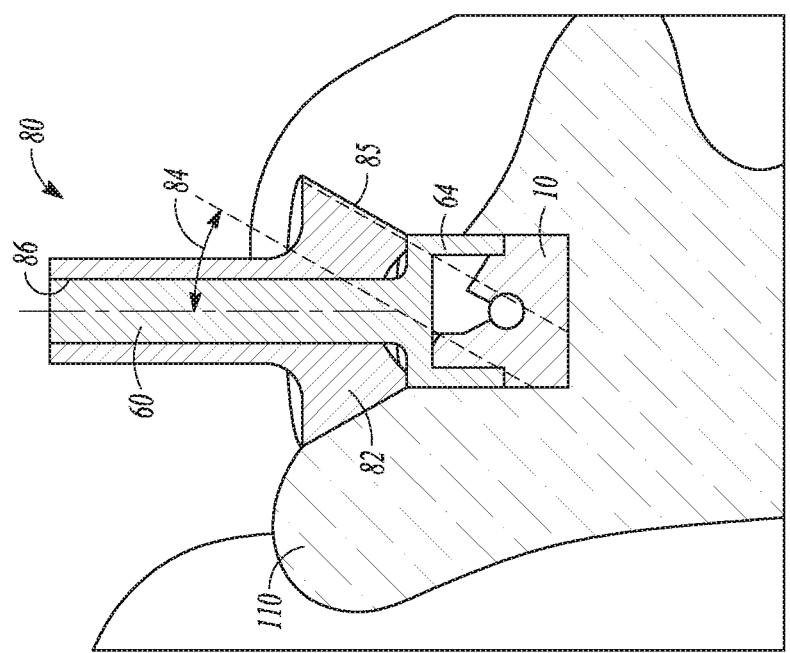
FIG. 5A is a cross-sectional view of the bushing of FIGS. 1A-D and the bushing inserter of FIGS. 3A-B being used with a cleanup reamer.

An optional cleanup reamer 80, shown in FIGS. 5A-B, can also be used with the above surgical instruments. Cleanup reamer 80 can have an inner bore 86 sized to receive shaft 62, 62' of bushing inserter 60, 60' and a cutting head 82. Cutting head 82 can have any cutting features configured to cut away bone, such as cutting flutes and/or sharp edges. Cutting head 82 can therefore form a drilling end of reamer 80. In an example, an external cutting surface 85 of cutting head 82 can form an angle 84 relative to shaft 62, 62' of bushing inserter 60, 60'. Angle 84 can be anywhere between about ten degrees (10°) to about fifty degrees (50°), and in an example is thirty degrees (30°). Angle 84 can be designed to cut away a particular amount of bone, as shown in FIG. 5B, to enable shaft 92 of reamer 90 to enter bore 12 of bushing 10 without contacting glenoid 110. In an example, bone can be removed from glenoid 110 at a posterior position so as to create a cutout 120 in glenoid 110 that facilitates insertion of shaft 92 of reamer 90 into bushing 10.

Figure 7B:
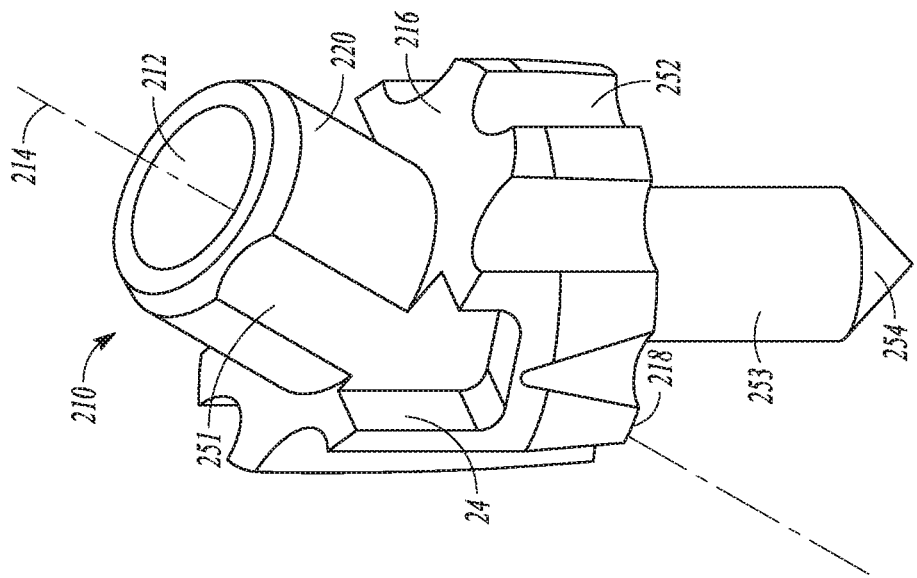
FIGS. 7A-B are opposing perspective views of an alternate bushing according to an example of the disclosure.
Figure 7A:
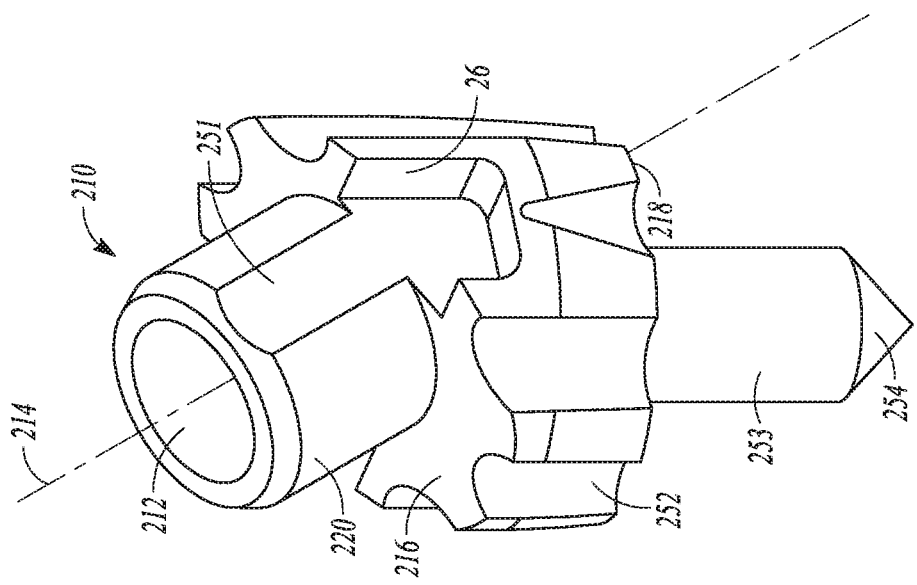
Figure 7C:
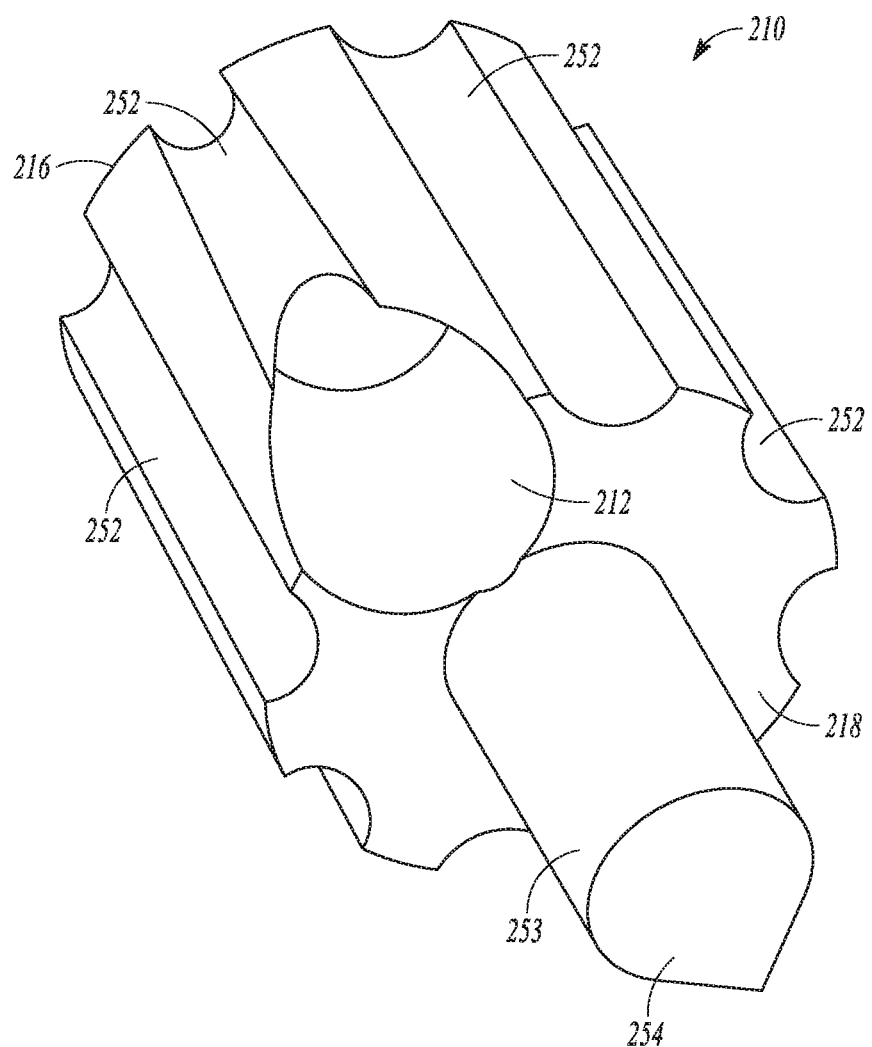
FIG. 7C is a bottom perspective view of the bushing of FIGS. 7A-B.

FIGS. 7A-C depict an alternate bushing 210. Here, similar reference numerals to bushing 10 are used for bushing 210, except in the 200 series, and the differences between bushings 10, 210 are predominantly discussed.

Bushing 210 can have a body 211 and a projection 220 that has an inner bore 212 extending along an axis 214. Unlike projection 20, projection 220 can have a single or multiple flats 251. Flats 251 can be used to interface with an insertion tool (e.g., bushing inserters 60, 60') that have a bore 66, 66' with like flats (not shown) for non-rotationally engaging with projection 220. Inner bore 212 of bushing 210 can have any of the angles of bore 12 of bushing 10 described above. In addition, although not shown, an offset can be provided with bushing 210 similar to offset 17 between axis 14 and central axis 15 of bushing 10.

Bushing 210 can also have a single or multiple cutouts 224, 226, as shown in FIGS. 7A-C, but can have an external surface with a number of protrusions 252 instead of threading. Of course, it is equally contemplated that threading instead of protrusions 252 could be used. Further, bushing 210 can have a shaft 253 extending from its bottom face 218. Shaft 253 can have a sharp tip or section 254 designed to puncture bone.

Referring to FIG. 2B, an example of a surgical method using the above surgical instruments can include first inserting a fixation pin 50 into glenoid 110. With fixation pin 50 in place, drill 30 and depth stop 40 can be inserted over fixation pin 50 via bore 32 of drill 30. Drill 30 can therefore be guided into a drilling position against glenoid 110. Drill 30 can then be rotated using a manual or powered driving instrument (not shown) so that its cutting section 34 drills into glenoid 110 and forms a bore in glenoid 110. As drill 30 is advanced, flange 38 of depth stop 40 can engage a portion of glenoid 110, for example the glenoid rim on the anterior aspect, and act to stop drilling of drill 30 to a certain depth. The depth to which drill 30 can be inserted is set forth above. After drilling, drill 30 and fixation pin 50 can be removed from glenoid 110.

Next, as shown in FIGS. 3A-B, bushing 10 can be inserted into the hole formed in glenoid 110 using drill 30. For instance, bushing inserter 60 can be attached to bushing 10 so that bushing 10 is substantially locked relative to bushing inserter 60, both rotationally and longitudinally, and bushing inserter 60 can be used to insert bushing 10 into the bone bore. For instance, arms 68 of bushing inserter 60 can engage with first and second cutouts 24, 26 of bushing 10. Alternatively, if bushing inserter 60' is used, a magnetic connection can be established between bushing 10 and bushing inserter 60' allowing bushing inserter 60' to be used to insert bushing 10 into the bone bore. In this instance, bushing 10 (e.g., projection 20 and/or top face 16) could have a single or multiple magnets and/or be formed of a magnetic material. If using bushing inserter 60, as shown in FIGS. 3A-B, bushing inserter 60 can be rotated to thread bushing 10 into the hole formed in glenoid 110. In particular, threads 22 of bushing 10 can engage the walls of the bone bore and act to thread bushing 10 into glenoid 110. If using bushing inserter 60', bushing 10 can either be threaded into glenoid 110 as discussed above, or it alternatively can be impacted into glenoid 110. In the case of impaction, bushing 10 could be unthreaded and could instead include other non-rotational fixation mechanisms that are more suited to impaction. For instance, bushing 10 could have circumferential ribs on body 11 that act to prevent unwanted back out of bushing 10 from glenoid 110. In this example, bushing 10 could be impacted using bushing inserter 60' by contacting bushing inserter 60' with a mallet or other impaction device to drive bushing 10 into glenoid 110.

The above steps can also be used to insert bushing 210 into a bore formed in glenoid 110. Indeed, either of bushing inserters 60, 60' could be used to insert bushing 210. Since bushing 210 can have protrusions 252 and not threads (although threads are contemplated), bushing 210 can be impacted into glenoid 110. Further, shaft 253 can be inserted into the hole in glenoid 110 and sharp tip 254 can penetrate glenoid 110 beyond the extent of the bone hole.

Referring to FIGS. 5A-B, if the procedure dictates, cleanup reamer 80 can then be used to make glenoid 110 more suitable for receiving reamer 90. For instance, cleanup reamer 80 can be inserted over shaft 62, 62' by way of its bore 86 and used to ream a part of glenoid 110 using cutting head 82. In an example, cutting head 82 can cut away part of glenoid 110 that corresponds to angle 84 of cutting head 82 so that reamer 90 can more easily engage with any of bushings 10, 210. As shown in FIG. 5A, angle 84 of cutting head 82 can correspond to the angle of bore 12, 212 of bushing 10, 210 as defined by axis 14, 214 so that shaft 92 of reamer 90 can travel through a trajectory that extends into bore 12, 212 without contacting or receiving interference from glenoid 110.

After insertion of bushing 10, 210 and/or clearing of bone using cleanup reamer 80, bushing inserter 60, 60' can be removed. As shown in FIGS. 6A-C, shaft 92 of reamer 90 can then be inserted into bore 12, 212 of bushing 10, 210 along axis 14, 214 and shaft 92 can be driven into glenoid 110, as shown in FIG. 6B. Since shaft 92 travels along bore 12, 214, the angle at which glenoid 110 is reamed can therefore be accurately set according to surgeon preference and/or as dictated by anatomical needs of the patient. Reamer 90 and in particular shaft 92 can be rotated within bore 12, 212 and advanced so that cutting face 94 of reamer 90 contacts glenoid 110 and reams the surface of glenoid 110, as shown in FIG. 6C. The surface of glenoid 110 can therefore be reamed at an appropriate angle and be configured to receive a prosthetic component (e.g., an augment).

In an example, a glenosphere in the case of a reverse shoulder procedure, or a concave glenoid component in the case of a traditional shoulder replacement, can be attached to glenoid 110 following reaming with reamer 90. For instance, a glenosphere can include, in some cases, multiple components—e.g., the concave glenosphere head, a baseplate, and an augment. An example of a glenosphere that is suitable for implantation in glenoid 110 after reaming as described herein is found in U.S. Patent Pub. No. 2016/0262902 to Winslow et al., owned by Biomet Manufacturing, LLC, which is incorporated herein by reference in its entirety. FIGS. 43-53 of the '902 Publication illustrate a baseplate or tray 300 with a central hole 304, bone screw apertures 316 surrounding central hole 304, and a peg 328. A bone screw can be inserted into central hole 304 through peg 328, and separate bone screws can be inserted into apertures 316 to affix tray 300 to the glenoid. As an example, it is contemplated that peg 328 of such a baseplate or tray 300 can be inserted into the bone hole formed in glenoid 110 after reaming with reamer 90, as detailed above. Thus, in this case the bone hole formed for bushing 10, 210 could serve to also receive peg 328 of baseplate or tray 300. Then, a screw could be inserted through central hole 304 into glenoid 110 and separate screws into apertures 316 to affix baseplate or tray 300 to glenoid 110. Additional components associated with tray 300, as described in the '902 Publication, could then be attached to tray 300 to form a glenosphere (or even a concave glenoid component as recognized in the '902 Publication). Thus, the location for peg 328 or a similar peg/post of a glenoid baseplate, similar to tray 300, can be established when the hole is drilled for bushing 10, 210 using drill 30, as shown in FIGS. 2A-B. This is yet another purpose for the present system of surgical components.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims. For example, the order of method steps or stages can be altered from that described above, as would be appreciated by a person of skill in the art.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

What is claimed is:

1. An orthopedic system comprising:
   an implantable body with an internal bore extending through the body, wherein the implantable body is sized and shaped so as to be insertable into a bore formed in bone, the implantable body being threaded, having an external projection configured to engage bone, or being configured to be press-fit into the bore formed in the bone to secure the implantable body in the bone; and
   a reamer having a cutting surface and a shaft, wherein the shaft is insertable into the internal bore of the body for guiding the reamer during reaming of a bone.

2. The orthopedic system of claim 1, wherein the body has a set of sidewalls and the internal bore is angled relative to the sidewalls.

3. The orthopedic system of claim 2, wherein the angle of the internal bore is anywhere between about 5-45°.

4. The orthopedic system of claim 1, wherein the cutting surface of the reamer comprises cutting teeth configured to cut away bone.

5. The orthopedic system of claim 1, wherein the implantable body has an external surface with at least a first projection configured to engage bone and prevent back-out of the implantable body when implanted.

6. The orthopedic system of claim 1, wherein the implantable body has a top face and a bottom face and the top face is angled relative to the bottom face.

7. The orthopedic system of claim 1, further comprising a drill having a cutting section that is sized and shaped to form a bore in bone that is substantially the same size and shape as the size and shape of the implantable body.

8. An orthopedic system comprising:
   an implantable body with an internal bore extending through the body and having at least one cutout comprising a channel extending along a sidewall of the implantable body;
   a reamer having a cutting surface and a shaft, wherein the shaft is insertable into the internal bore of the body for guiding the reamer during reaming of a bone;
   an inserter configured to attach to the implantable body and configured to drive the implantable body into a bore formed in the bone, wherein the inserter includes a shaft, an attachment head with a diameter greater than a diameter of the shaft, wherein the attachment head includes a bore sized to receive the bushing and at least one arm sized and shaped to be insertable into the at least one cutout of the implantable body, wherein the attachment head is configured to engage the implantable body and lock the implantable body to the inserter both longitudinally and rotationally; and
   a second reamer having a bore configured to receive the shaft of the inserter therein.

9. The orthopedic system of claim 8, wherein the internal bore is angled relative to the sidewall.

10. The orthopedic system of claim 9, wherein the angle of the internal bore is anywhere between about 5-45°.

11. The orthopedic system of claim 8, wherein the cutting surface of the reamer comprises cutting teeth configured to cut away bone.

12. The orthopedic system of claim 8, wherein the implantable body has an external surface with at least a first projection configured to engage bone and prevent back-out of the implantable body when implanted.

13. The orthopedic system of claim 8, wherein the implantable body is threaded, having an external projection configured to engage bone, or being configured to be press-fit into the bore in the bone to secure the implantable body in the bone.

14. The orthopedic system of claim 1, wherein the implantable body has a top face and a bottom face and the top face is angled relative to the bottom face.

15. The orthopedic system of claim 8, further comprising a drill having a cutting section that is sized and shaped to form the bore in the bone that is substantially the same size and shape as the size and shape of the implantable body.

16. The system of claim 8, wherein the bone is a glenoid and the internal bore of the implantable body is angled so as to guide the cutting surface of the reamer into the glenoid at an angle.

17. The system of claim 16, further comprising using a drill to form the bore in the bone to a depth that is dependent upon the angle of the internal bore of the implantable body.

18. The system of claim 17, further comprising forming the bone bore to a depth of anywhere between about 5-10 mm if the angle of the internal bore is anywhere between about 5-15°, forming the bone bore to a depth of anywhere between about 10-15 mm if the angle of the internal bore is anywhere between about 15-25°, or forming the bone bore to a depth of anywhere between about 12.5-17.5 mm if the angle of the internal bore is anywhere between about 25-35°.

19. The system of claim 8, wherein the implantable body is one of a plurality of implantable bodies each having an internal bore, wherein each of the internal bore is angled differently to correspond with a natural angle of an articulating surface of the bone.

* * * * *